United States Patent
Ali

(10) Patent No.: US 6,450,041 B1
(45) Date of Patent: Sep. 17, 2002

(54) CLAMP ASSEMBLY FOR A TESTING APPARATUS

(76) Inventor: Syed Waqar Ali, 13601 SW. 77th St., Miami, FL (US) 33183

( * ) Notice: Subject to any disclaimer, the term of this patent is extended or adjusted under 35 U.S.C. 154(b) by 0 days.

(21) Appl. No.: 09/902,383

(22) Filed: Jul. 10, 2001

(51) Int. Cl.[7] ................................................. G01N 3/02
(52) U.S. Cl. ...................................................... 73/856
(58) Field of Search .......................... 73/856, 857, 858, 73/859, 860, 855

(56) References Cited

U.S. PATENT DOCUMENTS

| | | | | |
|---|---|---|---|---|
| 3,835,697 A | * | 9/1974 | Schneider et al. | 73/159 |
| 4,043,185 A | * | 8/1977 | Siebert | 73/619 |
| 4,944,924 A | * | 7/1990 | Mawhirt et al. | 206/446 |
| 5,515,294 A | * | 5/1996 | Mohr et al. | 702/113 |
| 5,564,573 A | * | 10/1996 | Palm et al. | 209/518 |

* cited by examiner

Primary Examiner—Max Noori
(74) Attorney, Agent, or Firm—Robert M. Downey, P.A.

(57) ABSTRACT

In a testing apparatus used to observe the effects of positive pressure and vacuum pressure on a test specimen, such as the effects resulting from forces created by wind, explosions and water, a clamp system is provided for holding the test specimen against the apparatus in a manner which creates an airtight cavity between the test apparatus and the specimen. The clamp system includes one or more rolling clamp assemblies which are selectively movable in relation to the test apparatus in order to accommodate a range of sizes of specimens to be clamped at various locations on the test apparatus. Each clamp assembly includes an elongate track formed by spaced, parallel rails supported on a rolling trolley. One or more clamp members slidably carried on the track each include a threaded rod extending between the rails and a pivoting foot on the distal end of the rod for engaging the specimen. Upper and lower brace arms engage the test apparatus to prevent the track from moving away from the specimen and apparatus as the threaded rod is turned to advance the foot into engagement with the specimen until the specimen is held tightly against the test apparatus.

12 Claims, 4 Drawing Sheets

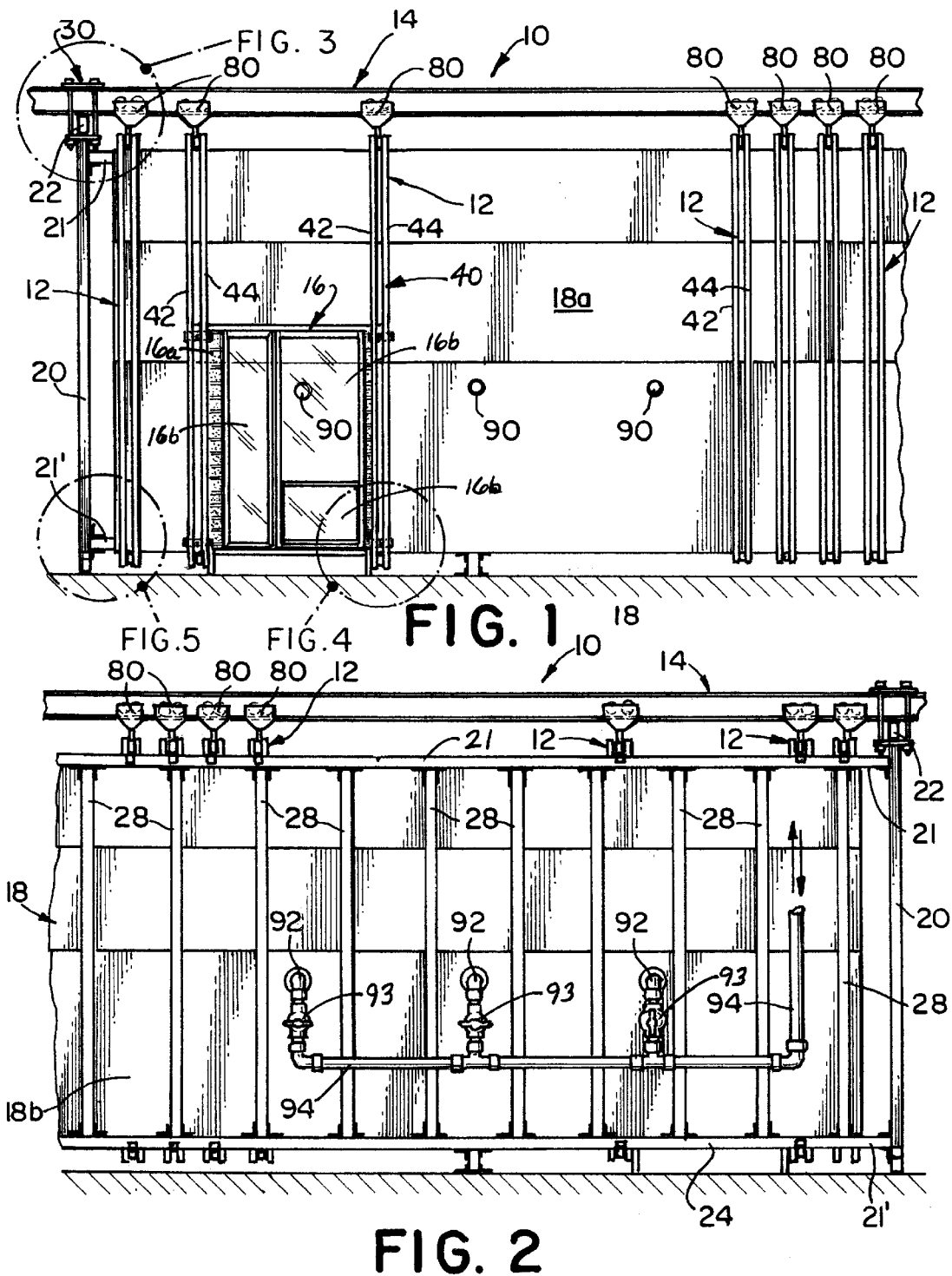

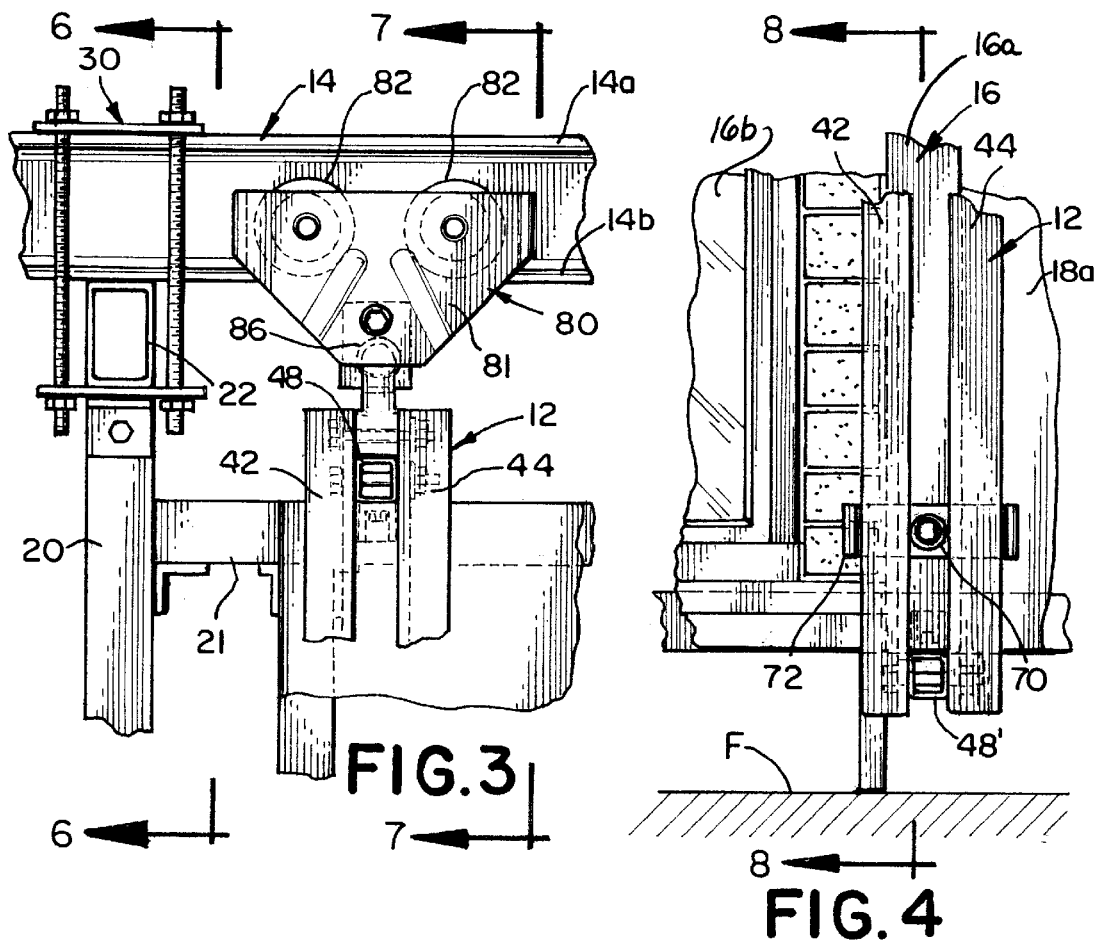
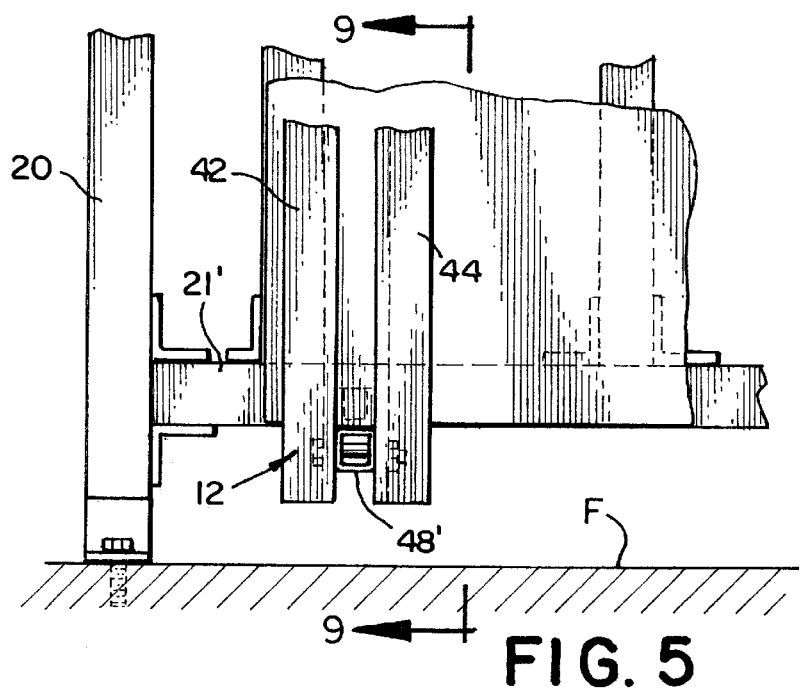

CLAMP ASSEMBLY FOR A TESTING APPARATUS

BACKGROUND OF THE INVENTION

1. Field of the Invention

The present invention relates to testing systems for observing the effects of positive pressure and vacuum and, more particularly, to a clamp system for use on a testing apparatus in order to hold a test specimen on the apparatus while observing the effects of positive pressure and/or vacuum, such as when conducting wind pressure, explosion, water and air infiltration tests on a specimen.

2. Discussion of the Related Art

In many industries, it is necessary to subject an article of manufacture to various tests in order to comply with industry and/or government imposed standards or regulations. Of particular relevance to the present invention is the need to subject a product, structural component or other article of manufacture to the effects of positive pressure and vacuum pressure. In certain situations, it is necessary to create a sealed cavity for introducing positive pressure or vacuum pressure in a test scenario in order to subject a test specimen to extreme pressure conditions. For example, current building codes in many jurisdictions throughout the United States and other countries require structures such as doors, windows, storm shutters and storm panels to undergo various tests which simulate hurricane-type conditions. Typically, this includes a cycling pressure test wherein the structure is subjected to rapid changes of pressure between atmospheric pressure and a defined maximum positive and/or negative pressure level throughout a series of repetitions.

In order to accomplish the pressure cycling test, as well as other tests for building structures required by present building codes, I have previously invented a Hurricane Simulation Testing Apparatus, which is described in detail in U.S. Pat. No. 5,505,091. My present invention, as disclosed herein, is designed for use in conjunction with my Hurricane Simulation Testing Apparatus as well as other Industrial testing systems which require a test specimen to be subjected to positive pressure and/or vacuum pressure. In particular, my present invention provides an efficient, versatile and highly effective means for clamping one or more test specimens to a testing apparatus in order to create and maintain an airtight, sealed cavity between the test apparatus and the one or more test specimens. More particularly, my present invention provides a clamp system including one or more rolling clamp assemblies which are easily and conveniently movable relative to a test apparatus and test specimen in order to accommodate for mounting of one or more test specimens of various sizes to select locations on the test apparatus.

SUMMARY OF THE INVENTION

The invention is directed to a clamp system for a testing apparatus used to observe the effects of positive pressure and vacuum pressure on a test specimen, such as the effects resulting from forces created by wind, explosions and water. Specifically, the clamp system is structured for holding the test specimen against the testing apparatus in a manner which creates an airtight cavity between the test apparatus and the specimen. The clamp assembly includes one or more rolling clamp assemblies which are selectively movable in relation to the test apparatus in order to accommodate a range of sizes of specimens to be clamped at various locations on the test apparatus. Each clamp assembly includes an elongate track formed by spaced, parallel rails supported on a rolling trolley. One or more clamp members slidably carried on the track each include a threaded rod extending between the rails and a pivoting foot on the distal end of the rod for engaging the specimen. Upper and lower brace arms engage the test apparatus to prevent the track from moving away from the specimen and apparatus as the threaded rod is turned to advance the foot into engagement with the specimen until the specimen is held tightly against the apparatus.

OBJECTS AND ADVANTAGES OF THE INVENTION

It is a primary object of the present invention to provide a clamp system for holding one or more test specimens against a surface of a test apparatus, and wherein the clamp system includes one or more clamp assemblies which are easily and conveniently moveable and positionable relative to the test specimen and test apparatus.

It is a further object of the present invention to provide a clamp system which is structured and disposed for holding one or more test specimens of various size and configuration to a surface of a test apparatus.

It is still a further object of the present invention to provide a clamp system which includes a plurality of clamp assemblies movably supported in relation to a surface of a test apparatus, and wherein the clamp assemblies are structured and disposed to permit simultaneous mounting of a plurality of test specimens on the test apparatus for independent testing thereof It is still a further object of the present invention to provide a clamp system for holding one or more test specimens against a surface of a test apparatus, and wherein the clamp system is structured and disposed to permit quick and efficient mounting and removal of the one or more test specimens in clamped engagement against the test apparatus.

It is still a further object of the present invention to provide a clamp system for holding a test specimen against a surface of a test apparatus, and wherein the clamp system quickly and efficiently adjusts to the size of the test specimen.

These and other objects and advantages of the present invention are more readily apparent with reference to the drawings and detailed description which follows.

BRIEF DESCRIPTION OF THE DRAWINGS

For a fuller understanding of the nature of the present invention, reference should be made to the following detailed description taken in conjunction with the accompanying drawings in which:

FIG. 1 is a front elevational view showing the clamp system of the present invention in relation to the front wall surface of a test apparatus, and wherein two clamp assemblies of the clamp system are shown operatively positioned for clamping a test specimen against the front wall surface of the test apparatus;

FIG. 2 is a rear elevational view of the clamp system and testing apparatus of FIG. 1 showing the rear side of the wall of the testing apparatus;

FIG. 3 is an isolated view taken from the area indicated as 3 in FIG. 1;

FIG. 4 is an isolated view taken from the area indicated as 4 in FIG. 1;

FIG. 5 is an isolated view taken from the area indicated as 5 in FIG. 1;

Like reference numerals refer to like parts throughout the several views of the drawings.

DETAILED DESCRIPTION OF THE PREFERRED EMBODIMENT

Figure 7:
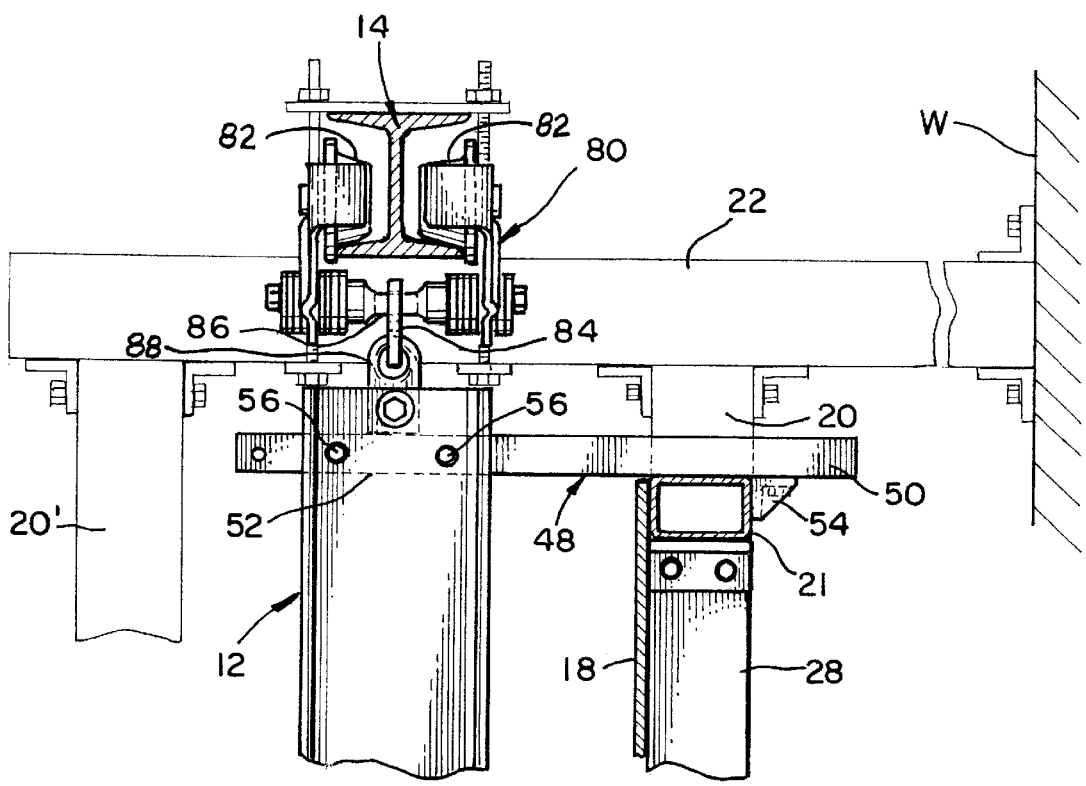
FIG. 7 is an isolated side elevational view, shown in partial cross-section, taken along the plane indicated by the line 7—7 of FIG. 3.

Referring to the several views of the drawings, and initially FIGS. 1 and 2, the clamp system of the present invention is shown and is generally indicated as 10. The clamp system 10 includes a plurality of clamp assemblies 12 movably carried on a horizontal I-beam 14 to enable transverse (e.g. left and right) movement of the clamp assemblies relative to a test wall 18 of a test apparatus 17. The clamp system is specifically structured for mounting one or more test pieces to the front surface 18a of the test wall 18. In the particular embodiment shown throughout several of the drawing figures, the test piece 16 includes an installation frame 16a which supports one or more test specimens 16b (e.g. a window, door, or storm shutter). As seen in FIGS. 1, 2, and 7, the horizontal I-beam 14 is supported above and forward of the test wall 18 so that the clamp assemblies 12 hang down from the supporting I-beam 14 in spaced relation to the front surface 18a of the test wall 18.

Figure 6:
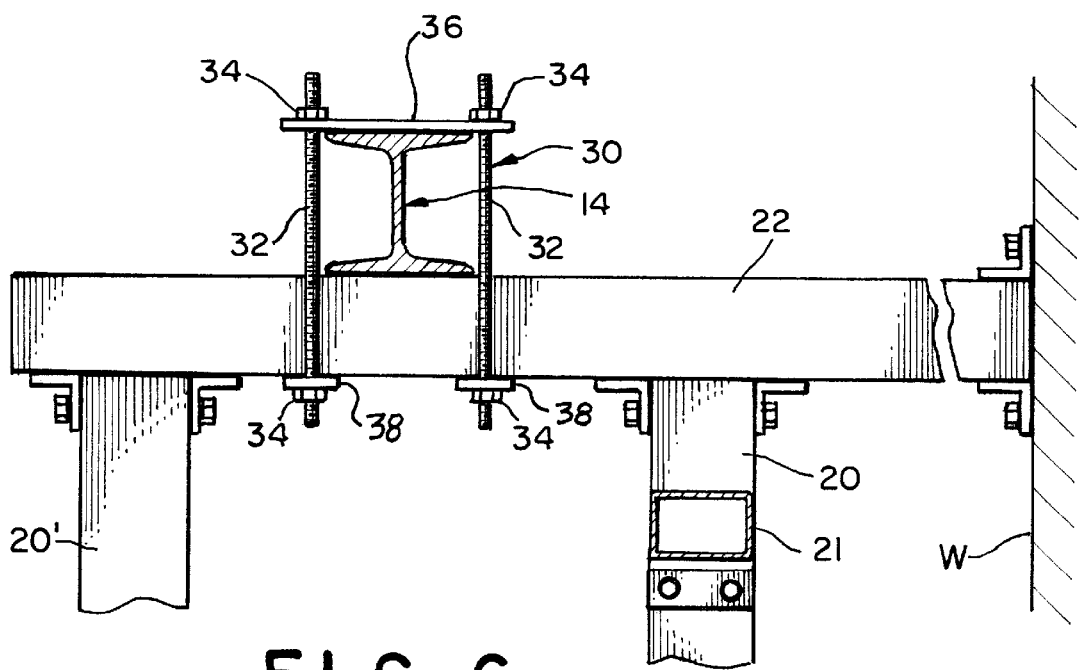
FIG. 6 is an isolated side elevational view, shown in partial cross-section, taken along the plane indicated by the line 6—6 of FIG. 3.

The test wall 18 and clamp system 10 are supported on a frame structure which is preferably secured to the Wall and Floor of a sturdy building structure. The supporting frame structure includes vertical frame members 20 anchored to the Floor and extending vertically to a horizontal cross beam 22. Outer vertical supports 20' are also anchored to the Floor at a position forward of the vertical frame members 20. The outer vertical supports 20' extend vertically upward to the horizontal cross beams 22 at opposite ends of the test wall 18. The horizontal cross beams 22 are anchored to the Wall of the building structure and are attached by braces to the vertical frame members 20 and outer vertical supports 20', as seen in FIG. 6. The frame structure further includes an upper horizontal wall frame member 21 secured to and spanning between the vertical frame members 20 at opposite ends of the test wall. A lower horizontal wall frame member 24 also is secured to and spans between the vertical frame members 20 in spaced relation above the Floor. Spaced, parallel vertical wall studs 28 extend between the upper and lower wall frame members 21, 24, in supporting engagement against the rear surface 18b of the test wall 18. Accordingly, the combination of the upper and lower wall frame members and the vertical wall studs 28 provide a supporting structure for mounting the test wall 18 thereto.

The horizontal I-beam 14 is mounted to the horizontal cross beams 22 and is adjustably positionable between the vertical frame members 20 and the outer vertical supports 20'. Specifically, an adjustable mounting assembly 30 secures the horizontal I-beam 14 to the tops of the horizontal cross beams 22 at selectively adjusted, fixed positions. The adjustable mounting assembly 30 includes a plurality of threaded steel rods 32 which extend through a pressure plate 36 on the top of the I-beam 14 and pressure plates 38 extending under the horizontal cross beams 22. Threaded fasteners, such as nuts 34, on opposite ends of the rods 32 are advanced towards the corresponding pressure plates 36, 38 to thereby squeeze the I-beam 14 between the top pressure plate 36 and the upper surface of the cross beams 22. Loosening of the nuts 34 at the lower ends of the steel rods 32 releases pressure on the horizontal I-beam 14, thereby permitting sliding movement of the horizontal I-beam to an adjusted position, either closer to or further away from the front surface 18a of the test wall 18.

Each of the clamp assemblies 12 includes a pair of spaced, parallel rails 42, 44 defining a clamp track for longitudinal movement and adjusted positioning of clamp members 60 carried on the rails 42, 44. An upper brace arm 48 extends generally perpendicularly from the rails 42, 44 and to a distal end portion 50 which is normally positioned behind the test wall 18. Specifically, the upper brace arm 48 extends from the top ends of the spaced parallel rails 42, 44 and over the upper horizontal wall frame member, terminating at the distal end portion 50 on the opposite, rear side of the test wall 18. A proximal end portion 52 is fixed between the spaced parallel rails 42, 44 at the upper ends thereof Specifically, bolt and nut fasteners 60 extend through the opposite rails 42, 44 and the upper brace arm 48 to thereby fix the brace arm to the rails, as best seen in FIG. 7.

A lower brace arm 48' is secured to the lower ends of the spaced parallel rails 42, 44 and extends generally perpendicularly therefrom and under the lower horizontal wall frame member, terminating at a distal end portion 50' behind the test wall 18. The lower brace arm 48' is secured using bolt and nut fasteners 56 in the same manner as described in connection with the upper brace arm 48. The distal end portions 50, 50' of the upper and lower brace arms 48, 48' are each fitted with stop members 54. In a preferred embodiment the stop members 54 are defined by a genuinely triangular or L-shaped steel brace and is structured and disposed for abutting, stopping engagement with the respective upper and lower horizontal wall frame members 21, 24 upon urging the rails 42, 44 of the clamp assembly away from the front surface 18a of the test wall 18. Accordingly, the brace arms 48, 48' and stop members 54 serve to limit outward movement of the rails 42, 44 of the clamp assemblies relative to the test wall 18.

Figure 8:
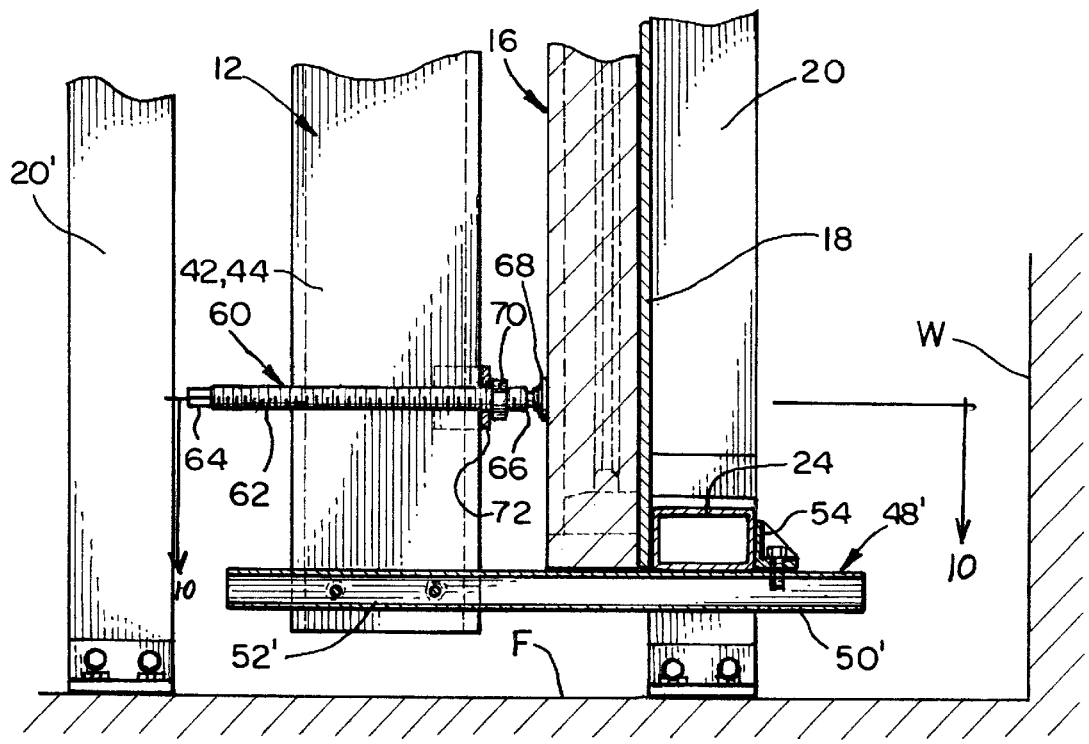
FIG. 8 is an isolated side elevational view, shown in partial cross-section, taken along the plane indicated by the line 8—8 of FIG. 4.
Figure 10:
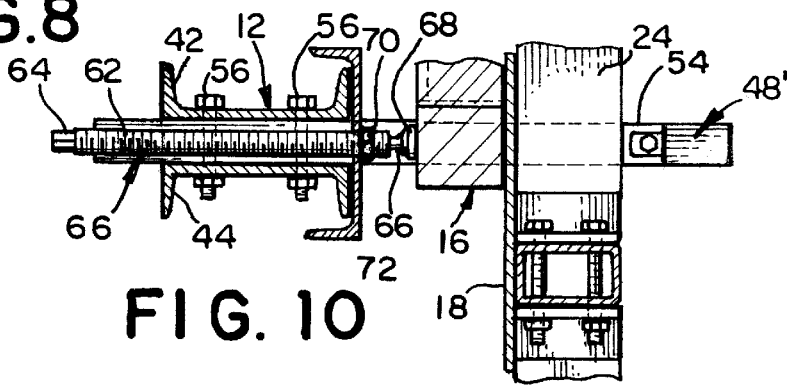
FIG. 10 is an isolated top plane view, shown in partial cross-section, taken along the line indicated as 10—10 of FIG. 8.
Figure 9:
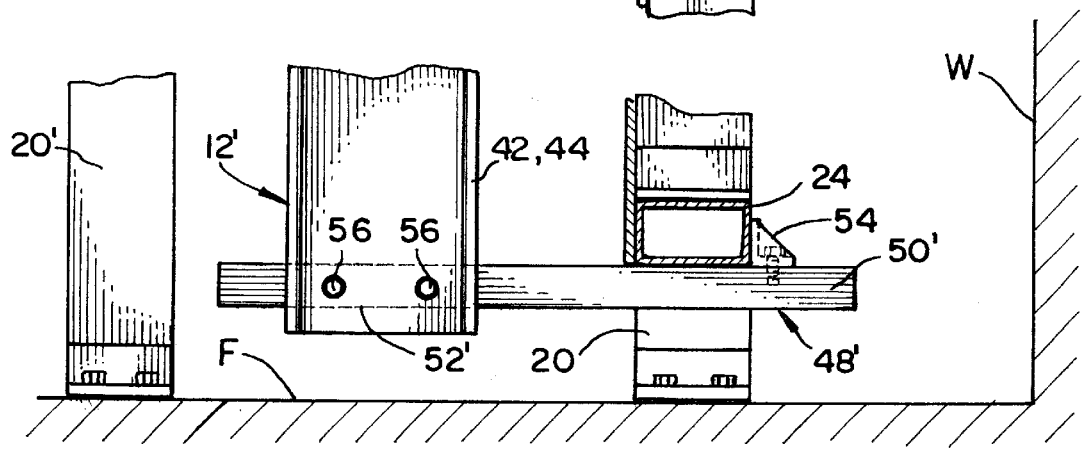
FIG. 9 is an isolated side elevational view, shown in partial cross-section, taken along the plane indicated by the line 9—9 of FIG. 5.

Each of the sets of spaced parallel rails 42, 44 of the respective clamp assemblies carries one or more clamp members 60. The clamp members 60 each include a threaded rod which extends between the respective parallel rails 42, 44 so that a multi-sided proximal end of the threaded rod 62 is positioned on the outer side of the rails (i.e. away from the test wall) and an opposite distal end 66 of the threaded rod 62 is positioned between the rails 42, 44 and the front surface 18a of the test wall 18. A pivoting foot 68 is secured to the distal end of the threaded rod of each clamp member and is structured and disposed for engagement with the test piece 16, as best seen in FIGS. 8 and 10. A retaining nut 70 on the distal end of the threaded rod secures a C-shaped brace 72 against an interfacing side of the parallel rails 42, 44 to thereby exert pressure on the rails 42, 44 as the pivoting foot 68 is urged against the test piece 16. This serves to push the rails 42, 44 outwardly relative to the test piece and the test wall so that the stop members 54 on the respective upper and lower brace arms 48, 48' engage the upper and lower horizontal frame members.

The track defined by the spaced parallel rails 42, 44 provides a means for longitudinal movement and adjusted positioning of the clamp members 60 relative to the test piece 16 and the test wall 18. More specifically, when the pivoting foot 68 is not pressed against the test piece 16, so that pressure of the C-shaped brace 72 against the rails 42, 44 is released, the clamp members 60 are able to be moved upwardly or downwardly along the rails 42, 44. This permits the clamp members to be moved into a selected position to accommodate for various size test pieces 16. For example, if the test piece 16 shown in FIG. 1 were removed and a taller test piece were to be replaced for testing, the position of the upper clamp members 60 could be quickly adjusted by raising them on the rails 42, 44 to a position closer to the top corners of the taller test piece. Similarly, all of the clamp members 60 could be moved higher on the rails if it were desired to position the test piece 16 higher on the test wall.

The clamp assemblies 12 are supported on the horizontal I-beam 14 so that they hang downwardly therefrom. Specifically, each of the clamp assemblies 12 connects to a rolling trolley 80 which is movably carried on the I-beam 14. The rolling trolley 80 associated with each of the clamp assemblies 12 includes trolley wheels 82 positioned on opposite sides of the I-beam and in rolling engagement with lower horizontal plate of the I-beam. Accordingly, the trolleys are able to travel along the length of the I-beam between the I-beam mounting assemblies 30 at the opposite ends of the test wall. A hanger 84 extends down from a hanger shaft 86 of the trolley and connects to a closed hook 88 bolted to the top of the rails 42, 44 of the clamp assembly. In this manner, the clamp assemblies 12 are able to hang from the respective trolleys 80 in a manner which permits the rails to swing towards and away from the test wall. By grabbing the parallel rails 42, 44 and pulling them to the left or the right, the trolley 80 is caused to travel along the I-beam, thereby permitting transverse movement and selective positioning of the clamp assemblies relative to the test wall and one or more test pieces 16 being mounted to the test wall.

As seen in FIGS. 1 and 2, the test wall is provided with a plurality of air passage holes 90. The clamp system of the present invention is specifically structured to hold the test piece 16 securely against the front surface 18a of the test wall 18 so that the installation frame 16a of the test piece surrounds at least one of the air passage holes 90. When the clamp members 60 are tightened against the installation frame, forcing the installation frame against the front surface 18a of the test wall, a sealed, airtight cavity is formed between the test specimen 16b and the test wall 18. Air conduit connections 92 fitted to the air passage holes 90 on the rear side of the test wall connect to air flow control valves 93 associated with each of the air passage holes 90. The air control valves 93 are connected to a main air flow conduit 94 which leads to a blower or other source for creating positive or negative air pressure. Accordingly, when the test piece 16 is mounted over one or more of the air passage holes 90 to create an airtight cavity between the test specimen and the front wall surface, the respective air flow control valve(s) 93 associated with the one or more air passage holes 90 is opened. This allows positive air pressure or negative air pressure to be created within the airtight cavity between the test specimen and the test wall. Specifically, positive air pressure can be introduced into the airtight cavity to a predetermined high pressure level and then cycled, according to testing standards, to observe the effects of high pressure on the test specimen. Likewise, negative air pressure can be created by removing air from the airtight cavity, creating a vacuum. The vacuum pressure can then be cycled between atmospheric pressure and a predetermined negative pressure level according to testing standards, while observing the effects of the negative pressure on the test specimen. It should be noted that other tests can be conducted, using the test apparatus disclosed, or other types of testing equipment, to observe the effects of positive and negative air pressure, such as those created by the forces of wind or explosions, as well as the effects of water pressure. Other tests, including water and air infiltration tests may be conducted using the clamp system of the present invention.

While the instant invention has been shown and described in accordance with a preferred and practical embodiment thereof, it is recognized that departures from the instant disclosure are contemplated within the spirit and scope of the invention, as set forth in the following claims and as interpreted under the doctrine of equivalents.

What is claimed is:

1. A clamp system for holding a test specimen against a surface of a test apparatus, said clamp system comprising:
    at least one clamp assembly including:
        a pair of spaced, parallel rails joined to one another and defining an elongate track having a first end portion and an opposite second end portion;
        at least one clamp member movably carried on said elongate track and including a rod extending between said parallel rails of said track and having a distal end maintained between said track and the surface of the test apparatus;
        said clamp member further including means for advancing and withdrawing said distal end of said rod relative to the surface of the test apparatus;
        said at least one clamp member further including engaging means on said distal end of said rod for engaging and applying pressure against the test specimen upon advancing the distal end in order to hold the test specimen against the surface of the test apparatus; and
        brace arms extending from said opposite first and second ends of said track, said brace arms being structured and disposed for engagement with the test apparatus to stop the track from moving away from the test specimen and the surface of the test apparatus as the engaging means of said at least one clamp member is advanced in forced engagement against the test specimen;
    transverse movement means for moving and selectively positioning said at least one clamp member relative to the test apparatus and the test specimen, said transverse movement means including:
        a trolley fixed to one of said first or second ends of said track and said trolley including at least one rotatable wheel; and
        an elongate rail supported in spaced, parallel relation to the surface of the test apparatus, said rail being structured and disposed for rolling engagement of said at least one wheel of said trolley therewith to thereby permit travel of said trolley along at least a portion of a length of said rail.

2. The clamp system as recited in claim 1 comprising:
    a plurality of said clamp assemblies.

3. The clamp system as recited in claim 2 comprising:
    a plurality of said clamp members movably carried on said elongate track of each of said plurality of clamp assemblies.

4. A clamp system for holding a test specimen against a surface of a test apparatus, said clamp system comprising:

at least one clamp assembly including:
  at least one clamp member having a distal end with engagement means thereon for engaging and applying pressure against the test specimen upon advancing the distal end of said clamp member toward the test specimen, to thereby hold the test specimen against the surface of the test apparatus;
  an elongate track having a first end portion and an opposite second end portion, said elongate track being structured and disposed to carry said at least one clamp member thereon and defining longitudinal movement means for moving said at least one clamp member along a longitudinal axis relative to the test specimen and the test apparatus; and
  brace arms extending from said opposite first and second ends of said track, said brace arms being structured and disposed for engagement with the test apparatus to stop the track from moving away from the test specimen and the surface of the test apparatus as the engagement means of said at least one clamp member is advanced in forced engagement against the test specimen;
transverse movement means for moving said at least one clamp member along a transverse axis relative to the test apparatus.

5. The clamp system as recited in claim 4 wherein said transverse movement means comprises:
  a trolley fixed to one of said first or second ends of said track and said trolley including at least one rotatable wheel; and
  an elongate rail supported in spaced, parallel relation to the surface of the test apparatus, said rail being structured and disposed for rolling engagement of said at least one wheel of said trolley therewith to thereby permit travel of said trolley along at least a portion of a length of said rail.

6. The clamp system as recited in claim 4 comprising:
a plurality of said clamp assemblies.

7. The clamp system as recited in claim 6 comprising:
a plurality of said clamp members carried on each of said elongate tracks of plurality of clamp assemblies.

8. A clamp system for holding a test specimen against a surface of a test apparatus, said clamp system comprising:
at least one clamp assembly comprising:
  at least one clamp member having a distal end with engagement means thereon for engaging and applying pressure against the test specimen upon advancing the distal end of said clamp member toward the test specimen, to thereby hold the test specimen against the surface of the test apparatus;
  an elongate track having a first end portion and an opposite second end portion, said elongate track being structured and disposed to carry said at least one clamp member thereon and defining longitudinal movement means for moving said at least one clamp member along a longitudinal axis to the test specimen and the test apparatus;
  means for advancing and withdrawing the distal end of said clamp member relative to the test specimen; and
  brace means for stopping said elongate track from moving away from the test specimen and the surface of the test apparatus as said engagement means of said at least one clamp member is advanced into forced engagement against the test specimen; and
transverse movement means for moving said at least one clamp member along a longitudinal axis relative to the test apparatus.

9. The clamp system as recited in claim 8 wherein said elongate track comprises a pair of spaced, parallel rails joined to one another and being structured and disposed to permit sliding, adjusted movement of said at least one clamp member along at least a portion of a length of said spaced, parallel rails.

10. The clamp system as recited in claim 9 wherein said transverse movement means comprises:
  a trolley fixed to one of said first or second ends of said spaced, parallel rails and said trolley including at least one rotatable wheel; and
  an elongate rail supported in spaced, parallel relation to the surface of the test apparatus, said rail being structured and disposed for rolling engagement of said at least one wheel of said trolley therewith to thereby permit travel of said trolley along at least a portion of a length of said rail.

11. The clamp system as recited in claim 10 comprising:
a plurality of said clamp members.

12. The clamp system as recited in claim 11 further comprising:
a plurality of said pairs of spaced, parallel rails, defining a plurality of said elongate tracks, and each of said pairs of spaced, parallel rails defining a plurality of said clamp members thereon.

* * * * *